United States Patent [19]

Kira et al.

[11] Patent Number: 5,428,656
[45] Date of Patent: Jun. 27, 1995

[54] APPARATUS AND METHOD FOR FLUORESCENT X-RAY ANALYSIS OF LIGHT AND HEAVY ELEMENTS

[75] Inventors: Akimichi Kira; Yoshimichi Sato, both of Kyoto, Japan

[73] Assignee: Horiba, Ltd., Kyoto, Japan

[21] Appl. No.: 133,575

[22] Filed: Oct. 8, 1993

[30] Foreign Application Priority Data

Oct. 11, 1992 [JP] Japan .................................. 4-299289

[51] Int. Cl.[6] .......................................... G01N 23/223
[52] U.S. Cl. ............................................ 378/45; 370/44
[58] Field of Search ...................... 378/45, 44, 46, 47, 378/48, 49, 50, 156

[56] References Cited

U.S. PATENT DOCUMENTS 4,815,116  3/1989  Cho ...................................... 378/45

*Primary Examiner*—David P. Porta
*Attorney, Agent, or Firm*—Price, Gess & Ubell

[57] ABSTRACT

A method and apparatus for measuring fluorescent X-rays from a sample include an X-ray voltage tube having a variable applied voltage during the measurement cycle. The resulting fluorescent X-rays are measured by a detector that output representative signals. The representative signals are used to calculate a characteristic energy spectrum which can be displayed to an operator. The use of a varying voltage ensures detecting both light and heavy elements. An X-ray filter can also be inserted to prevent any characteristic X-rays from being generated from the X-ray gun itself.

7 Claims, 5 Drawing Sheets

5,428,656

APPARATUS AND METHOD FOR FLUORESCENT X-RAY ANALYSIS OF LIGHT AND HEAVY ELEMENTS

BACKGROUND OF THE INVENTION

1. Field of the Invention

The present invention relates to a fluorescence qualitative analytical apparatus and method of analyzing elements contained in a sample and, more particularly, to an efficient method and apparatus for measuring both light and heavy elements in a sample, while avoiding any false signals that can be generated from an X-ray target.

2. Description of Related Art

The ability to analyze the constituent elements, for example, of both light and heavy metal elements in a sample, is valuable in industries and laboratories.

Since technicians sometimes deal with samples containing unknown elements of both a relatively small atomic number, such as Na, Mg, Al, Si, P, S, and Cl, having atomic number of 11, 12, 13, 14, 15, 16, and 17, respectively, and also of elements having relatively larger atomic numbers, for example, Sr, Y, Zr, Nb, Mo, Pd, Ag, In, Sn, Sb, W, Pt, Au, and Pb, having atomic numbers of 38, 39, 40, 41, 42, 46, 47, 49, 50, 51, 74, 78, 79, and 82, respectively, difficulties frequently occur in achieving accuracy in measuring each of the elements that are the constituent parts of the sample.

X-ray analyzers have been developed that generate a stream of electrons of high energy to contact a target which, in turn, emits primary X-rays. The primary X-rays, in turn, will contact a sample to generate fluorescent X-rays which are subsequently measured to determine the elements contained in the sample. The primary X-rays, however, can also be scattered by contacting the sample and can have nearly the same energies as the applied primary X-rays.

In addition, the target material of the X-ray target can also generate characteristic X-rays represented by that specific target material. For example, referring to FIG. 8, an intensity versus X-ray energy curve is disclosed for a target material containing rhodium (Rh), with the target producing a continuous band of X-rays, including an Rh-L X-ray which is characteristic of the X-rays of rhodium. The applied voltage in this condition is 15 kV.

FIG. 9 discloses another graph of a target containing rhodium, subject to an X-ray tube voltage of 50 kV. In FIG. 9, the continuous X-rays produced are shown along with the characteristic X-rays of rhodium, including an Rh-L ray, an Rh-K α, and an Rh-K ⊕ ray.

The target can have a characteristic element which will generate its own energy spectrum which can also be received by the detectors attempting to measure the fluorescent X-rays from the sample. For example, if the target contains rhodium (Rh), a measurement output can have the characteristic shown in FIG. 4, wherein the sample disclosing aluminum and copper, could mistakenly be judged to include rhodium as a component. The operator would not know whether the sample contains rhodium or whether this was a characteristic of the target which was perceived in the analysis of the X-rays coming apparently from fluorescent X-rays from the sample. As a result, it can become difficult to carry out a highly accurate quantitative analysis by a technician. The prior art is accordingly seeking an economical method and apparatus to avoid such problems.

SUMMARY OF THE INVENTION

The present invention provides an X-ray measurement method and apparatus for applying X-rays generated from a target to an X-ray tube to a sample containing both light and heavy elements. The X-ray tube can be responsive to a varying voltage over a predetermined range. The X-ray tube can also be removably fitted with an X-ray filter capable of blocking characteristic X-rays of material contained in the target. A sample station is provided for positioning the sample and the X-rays are provided at an angle to the sample for the purposes of generating fluorescent X-rays-characteristic of the elements in the sample. The voltage applied to the X-ray tube is varied from a relative low to a high range, while continuously subjecting the sample to X-rays generated from the target. A detector measures the X-rays and provides corresponding electric signals that then can be applied to a multi-channel analyzer through an amplifier to obtain an energy spectrum. This characteristic energy spectrum can then be outputted and displayed as a continuum graph across the varied applied voltage range.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide an apparatus and method for fluorescent X-ray analysis of light and heavy elements.

Figure 1:
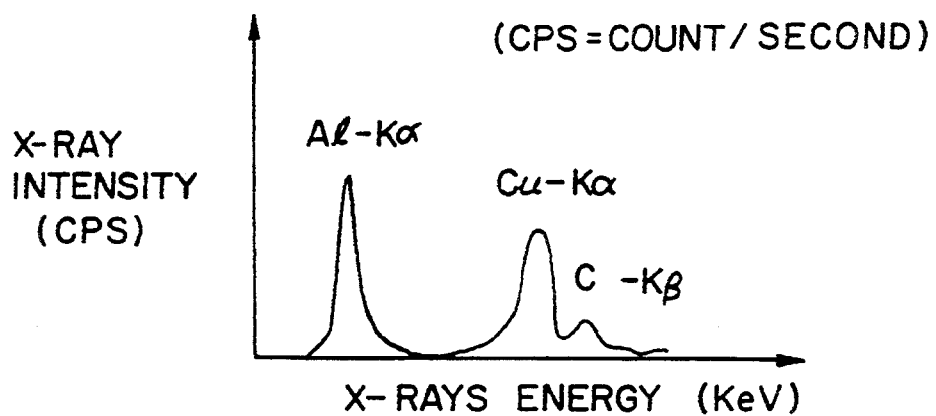
FIG. 1 is a diagram showing an energy spectrum of light elements contained in the sample obtained by a qualitative analytical method according to a first preferred embodiment of the present invention.

Referring to FIG. 1, a graph measuring the intensity of fluorescent X-rays (having an energy of 1.486 keV), which is generated by aluminum (Al) is disclosed when a 15 kV voltage is applied to the X-ray tube. This graph shows the sample containing not only aluminum but coexisting elements contained in the sample. During such a measurement, the energy value of the fluorescent X-rays 4 (FIG. 6) is fixed for each element contained in the sample, as shown in FIG. 1, so that the spectrum data have peaks at energy positions corresponding to the elements contained in the sample to be measured. A person skilled in this field can determine the elements specified from the particular positions of the peaks shown in FIG. 1.

Figure 2:
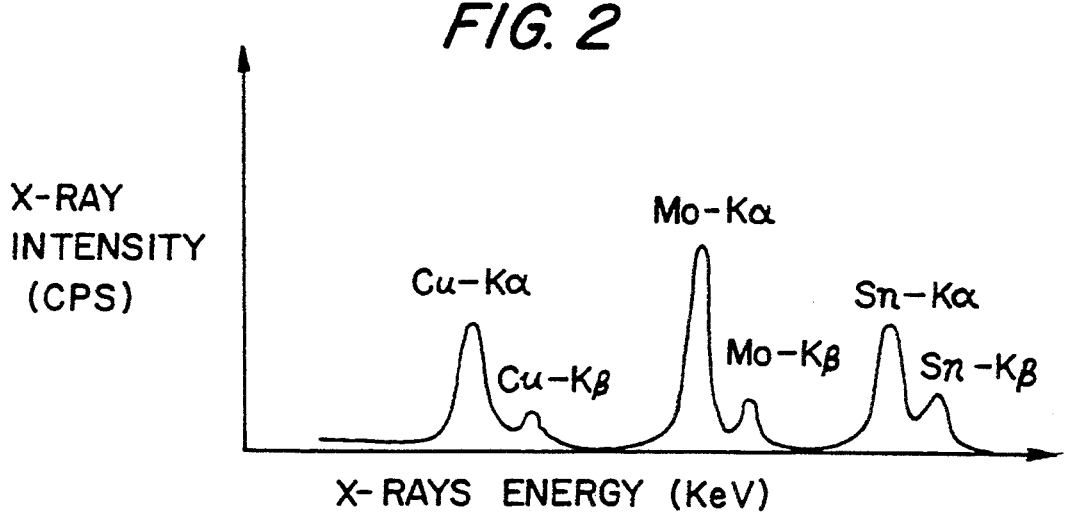
FIG. 2 is a diagram showing an energy spectrum of heavy elements obtained by a qualitative analytical method according a first preferred embodiment of the present invention.

Reference can be made to FIG. 2 to show the application of a higher tube voltage E of 50 kV applied to the same sample. When the higher tube voltage is applied it is difficult to achieve any reading to enable the determination of the Al-K α characteristic. Conversely, when comparing the graphs of FIGS. 1 and 2, it can be seen that the heavier elements, such as Mo-K α and Mo-K β and Sn-K α and Sn-K β cannot be determined at the lower X-ray tube voltage of 115 kV.

Figure 6:
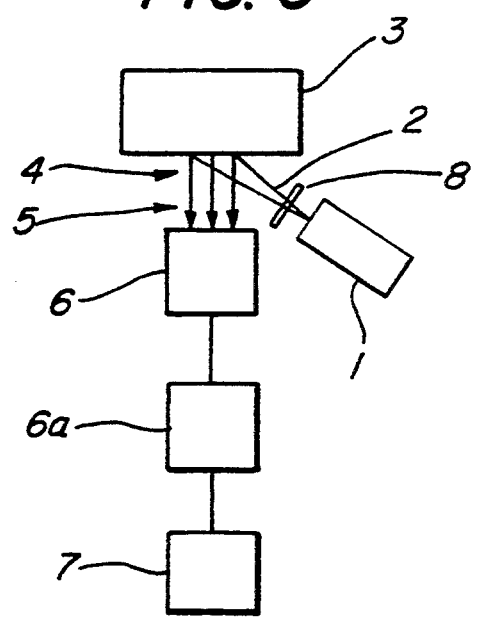
FIG. 6 is a schematic diagram showing an example of an analyzer using the quantitative analytical method according to the present invention.

Referring to FIG. 6, a schematic diagram of an instrument for measuring fluorescent X-rays is disclosed having an X-ray tube 1 generating primary X-rays 2 for application to a sample 3. The primary X-rays 2 can excite atoms in the sample 3 to generate fluorescent X-rays 4. The primary X-rays 2, however, can also be scattered by the sample target 3 and will have nearly the same energy as the initial primary X-rays. These scattered X-rays are symbolically shown as X-rays 5 mixed with the fluorescent X-rays 4. Both the fluorescent X-rays 4 and the scattered X-rays 5 emitted from the sample 3 are measured by a detector, such as a semiconductor detector 6, to be turned into appropriate representative electrical signals. These electrical signals are then applied to an amplifier 6a and subsequently to a multi-channel analyzer 7, such as computer-based instrument that can provide both a display and a printed hard copy of an energy spectrum.

Figure 7:
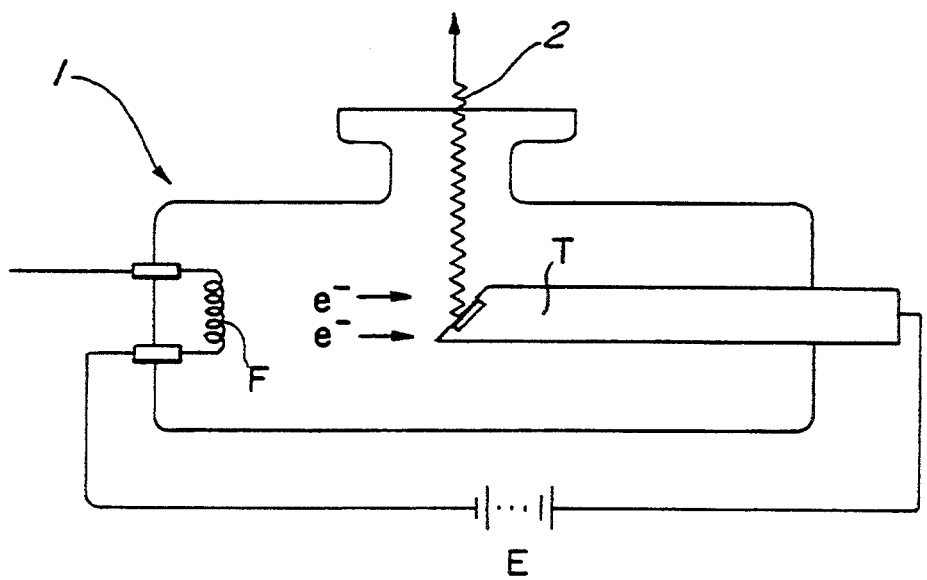
FIG. 7 is a schematic diagram showing the principal parts of the analyzer used in the analytical method according to the present invention.
Figure 8:
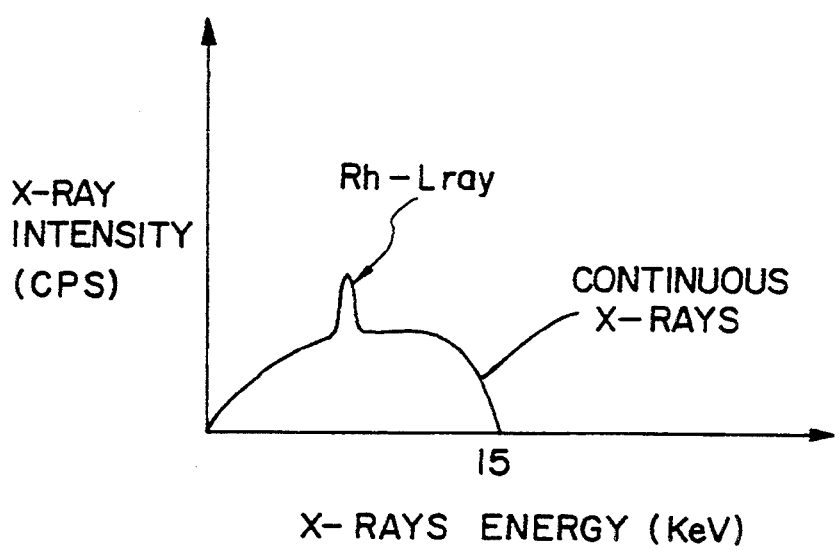
FIG. 8 is a diagram shown characteristics of a constituent material of an analyzer used in the analytical method according to the second preferred embodiment.
Figure 9:
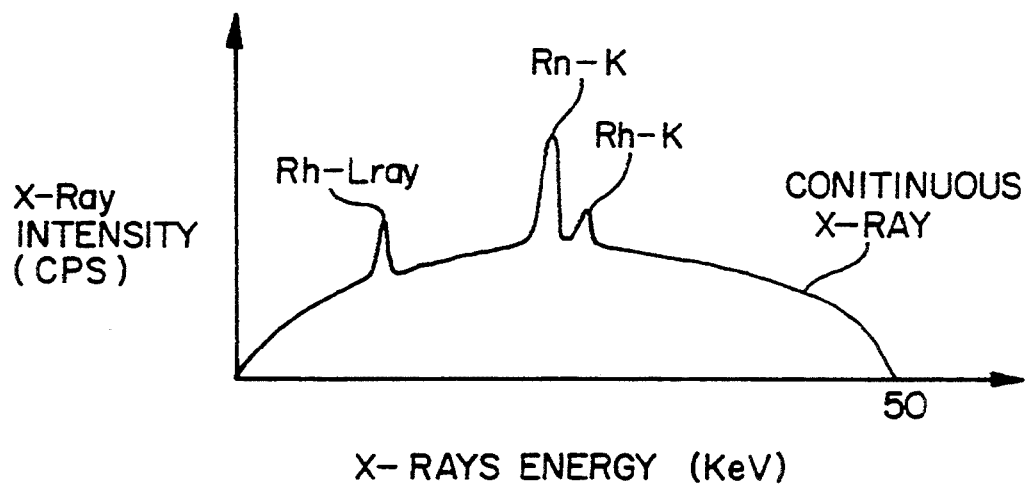
FIG. 9 is a diagram showing other characteristics of the constituent material of the analyzer used in the analytical method according to the second preferred embodiment.

Referring to FIG. 7, a schematic of the X-ray tube 1 is disclosed having a filament F that can be excited to generate electrons e- by the application of a tube voltage E. The tube voltage E can be a varying voltage, e.g., from 15 kV to at least 50 kV to vary the electrons that are accelerated from the filament F to be applied to a target T. Primary X-rays 2 are generated upon the application of the electrons E to the target portion. The target can be made, for example, of rhodium (Rh).

Energy spectra of light elements contained in the sample 3 (FIG. 6) to be measured, for example, Al are obtained as spectrum data by the use of a lower tube voltage E of 15 kV, as shown in FIG. 1, and heavy elements, such as Mo and Sn, are detected by using a higher tube voltage E of 50 kV, as shown in FIG. 2. The light elements and heavy elements contained in the samples can be measured by adding the spectrum data shown in FIG. 1 to the respective energy spectra shown in FIG. 2 to provide the combined graph shown in FIG. 3.

Figure 4:
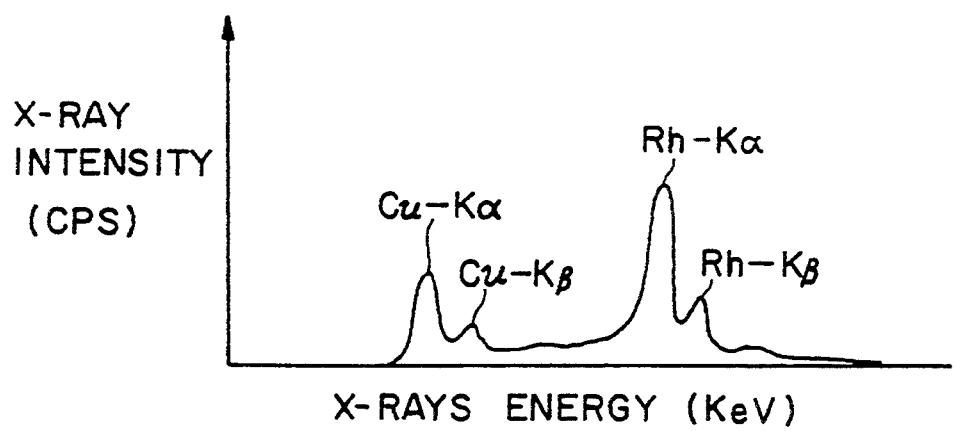
FIG. 4 is a diagram showing an energy spectrum of the sample to be measured obtained by an quantitative analytical method according to a second preferred embodiment of the present invention without using an X-ray filter.
Figure 5:
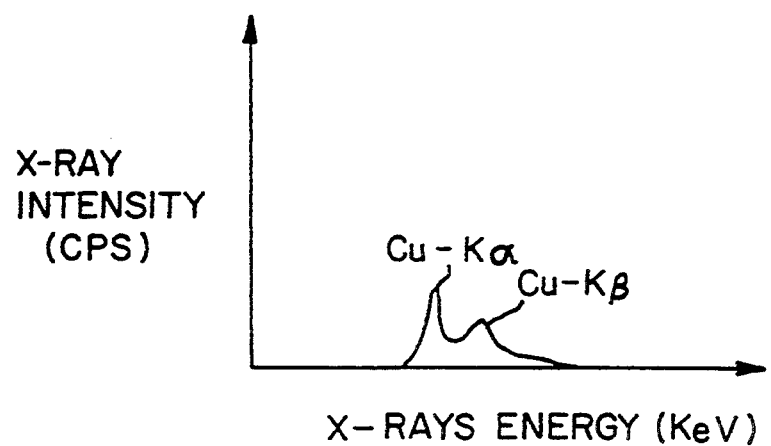
FIG. 5 is a diagram showing an energy spectrum of the respective elements contained in the sample to be measured obtained by the quantitative analytical method according a second preferred embodiment using a primary X-ray filter.

FIGS. 4 and 5 show a second preferred embodiment of the present invention in which it can be judged by using an X-ray filter 8 (primary X-ray filter) whether elements contained in the target material (Rh) of the X-ray tube 1 are also contained in the sample to be measured or not.

In the case where Rh is used as the target material of an X-ray tube 1 (FIG. 6), the X-ray filter 8 prevents characteristic X-rays emitted from the target material of the X-ray tube 1 from being incident upon the sample 3 when the filter 1 is arranged between the X-ray tube 1 and the sample 3. The spectrum of Rh appears, as shown in FIG. 4, in the case where the primary X-ray filter 8 is not used, but the spectrum data of an Rh element does not appear if the primary X-ray filter 8 is used, as shown in FIG. 5. Thus, it can be judged in the spectrum data, as shown in FIG. 4, that the characteristic X-rays of Rh are generated from the sample 3 to be measured and not from the target material when the filter 8 is used.

In a plurally conditioned fluorescent X-ray qualitative analytical method according to the present invention, light elements and heavy elements contained in the sample 3 are measured by making a tube voltage E variable, while applying primary X-rays emitted from an X-ray tube 1 to the sample 3, detecting the fluorescent X-rays emitted from the sample to be measured by a detector and reading the resulting signals as an energy spectrum through signal-treating means 7.

Figure 3:
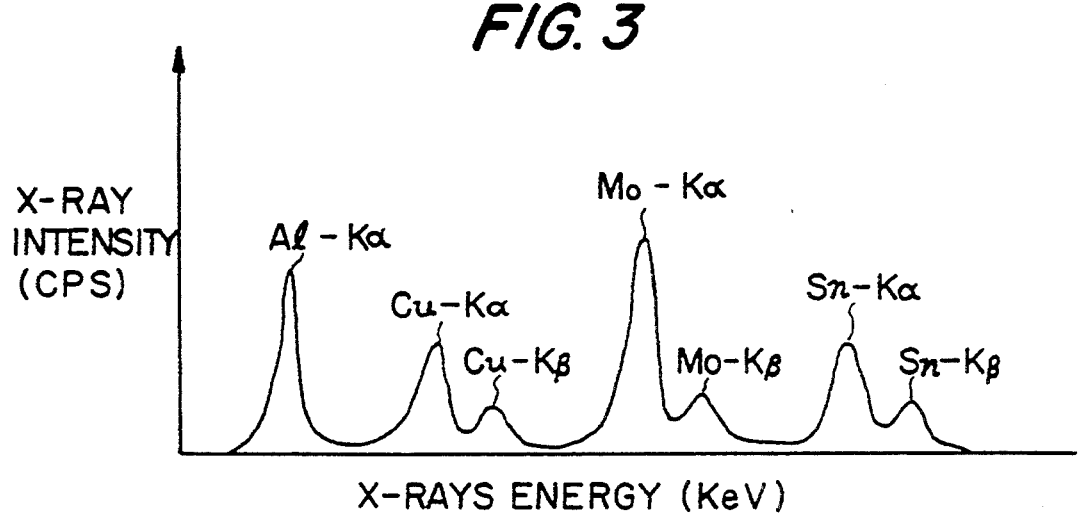
FIG. 3 is a diagram showing an energy spectrum of light elements and heavy elements contained in a sample to be measured obtained by a qualitative analytical method according to the first preferred embodiment of the present invention.

In the case where the light and heavy elements contained in the sample to be measured are detected under at least two conditions where the tube voltage of the X-ray tube 1 is low and high, the energy spectrum of the light elements, for example Al, is obtained as spectrum data by the use of the low tube voltage E of 15 kV, as shown in FIG. 1, and the heavy elements, such as Mo and Sn, are detected by use of the high tube voltage E of 50 kV, as shown in FIG. 2. In addition, the light and heavy elements contained in the sample to be measured can also be detected by adding the spectrum data shown in FIG. 1 to the respective energy spectrum of data shown in FIG. 2, as shown in FIG. 3.

The setting of the tube voltage E is not limited by two conditions of a tube voltage low and high and the tube voltage may be suitably set to a plurality of conditions depending upon the kind of sample to be measured in order to carry out a qualitative analysis with high accuracy.

The present invention provides a plurally conditioned fluorescent X-ray qualitative analytical method, in which an X-ray filter (primary X-ray filter) can be selectively inserted to prevent characteristic X-rays of at least a target material from being incident upon the sample 3, whereby the effect of the elements contained in the target material of the X-ray tube 1 can be blocked. In the case where Rh is used as a target material of the X-ray tube 1, the X-ray filter 8 can prevent the characteristic X-rays emitted from Rh of the X-ray tube 1 from being incident upon the sample 3. Thus, without the filter 8, the energy spectrum of Rh from the X-ray target could appear, as shown in FIG. 4, while, in the case where the primary X-ray filter 8 is used, it is removed from the spectrum data, as shown in FIG. 5, so that it can be concluded that an Rh element is not actually contained in the sample 3. Conversely, if an Rh characteristic spectrum shows with the filter 8, then the operator knows it is only from the sample 3.

According to the present invention, the X-ray filter can be suitably selected depending upon a kind of the target material of the X-ray tube.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An X-ray measurement method for applying X-rays generated from a target in an X-ray tube to a sample which contains light and heavy elements, comprising the steps of:
   positioning the sample to receive the X-rays from the X-ray tube;
   varying an applied voltage, between at least an upper and a lower level, to the X-ray tube while subjecting the sample to X-rays generated by the application of the voltage, the upper level corresponding to heavy metals and the lower level corresponding to light levels;
   measuring the fluorescent X-rays emitted from the sample as a result of the impact of X-rays from the X-ray tube for the at least two different levels of voltage and providing measurement signals;
   calculating a characteristic energy spectrum from the measurement signals; and
   outputting the calculated energy spectrum.

2. An X-ray measurement method of claim 1 further including a step of displaying the calculated energy spectrum as a continuum graph across the applied voltage range.

3. An X-ray measurement method of claim 2 further including a step of filtering the X-rays from the X-ray tube to block any characteristic energy spectrum from an element of the target.

4. An X-ray measurement apparatus for applying X-rays generated from a target in an X-ray tube to a sample which contains light and heavy elements, comprising:
   means for positioning the sample to receive the X-rays from the X-ray tube;
   means for varying an applied voltage, between at least an upper and a lower level, to the X-ray tube while subjecting the sample to X-rays generated by the application of the voltage, the upper level corresponding to heavy metals and the lower level corresponding to light levels;
   means for measuring the fluorescent X-rays emitted from the sample as a result of the impact of X-rays from the X-ray tube for the at least two different levels of voltage and providing measurement signals;
   means for calculating a characteristic energy spectrum from the measurement signals; and
   means for outputting the calculated energy spectrum.

5. An X-ray measurement apparatus of claim 4 further including means for displaying the calculated energy spectrum as a continuum graph across the applied voltage range.

6. An X-ray measurement method for applying X-rays generated from a target in an X-ray tube to a sample which contains light and heavy elements, comprising the steps of:
   positioning the sample to receive the X-rays from the X-ray tube;
   alternatively positioning an X-ray filter between the X-ray tube and the sample to selectively prevent characteristic X-rays that are generated by a component material of the target from contacting the sample;
   applying voltage to the X-ray tube while subjecting the sample to X-rays generated by the application of the voltage;
   measuring the fluorescent X-rays emitted from the sample as a result of the impact of X-rays from the X-ray tube for at least two different levels of voltage and providing measurement signals;
   calculating a characteristic energy spectrum from the measurement signals; and
   outputting the calculated energy spectrum.

7. An X-ray measurement apparatus for applying X-rays generated from a target in an X-ray tube to a sample which contains light and heavy elements, comprising:
   means for positioning the sample to receive the X-rays from the X-ray tube;
   means for alternatively positioning an X-ray filter between the X-ray tube and the sample to selectively prevent characteristic X-rays that are generated by a component material of the target from contacting the sample;
   means for applying voltage to the X-ray tube while subjecting the sample to X-rays generated by the application of the voltage;
   means for measuring the fluorescent X-rays emitted from the sample as a result of the impact of X-rays from the X-ray tube for at least two different levels of voltage and providing measurement signals;
   means for calculating a characteristic energy spectrum from the measurement signals; and
   means for outputting the calculated energy spectrum.

* * * * *